United States Patent [19]

Früngel

[11] Patent Number: 4,515,477
[45] Date of Patent: May 7, 1985

[54] VISIBILITY METER AND COMPONENTS USED THEREIN

[76] Inventor: Frank Früngel, Im Glockenacker 2, 8053 Zürich, Switzerland

[21] Appl. No.: 510,743

[22] Filed: Jul. 5, 1983

Related U.S. Application Data

[63] Continuation of Ser. No. 196,145, Oct. 10, 1980, abandoned.

[30] Foreign Application Priority Data

Feb. 10, 1979 [CH] Switzerland ............... 8850/79

[51] Int. Cl.³ .................................................. G01N 21/00
[52] U.S. Cl. ................................................ 356/338; 313/611
[58] Field of Search ............... 356/337, 338, 339, 340, 356/341, 342, 343; 313/110, 204, 220, 224, 611, 618; 250/574

[56] References Cited

U.S. PATENT DOCUMENTS

| | | | |
|---|---|---|---|
| 3,510,666 | 5/1970 | Topol | 250/574 |
| 3,817,623 | 6/1974 | Fruengel | 356/338 |
| 4,099,178 | 7/1978 | Ranney et al. | 250/574 X |
| 4,432,645 | 2/1984 | Früngel | 356/338 |

Primary Examiner—Davis L. Willis
Assistant Examiner—Matthew W. Koren
Attorney, Agent, or Firm—Michael J. Striker

[57] ABSTRACT

A discharge lamp with high intensity and high local stability is disclosed, which is suitable for use as a light source in a visibility meter. A light receiver also suitable for use in a visibility meter is disclosed. The discharge lamp has a discrete anode chamber and a discrete cathode chamber which are both filled with gas and which are interconnected via a capillary tube. One end of the capillary tube is adjacent a cathode located within the cathode chamber, while the other end of the capillary tube projects forwardly of a region in which the anode is adjacent the capillary tube. Plasma is confined within the capillary tube, resulting in high local stability and high intensity light output. The light receiver utilizes a photosensitive element and an electrical filter which is so designed that response of the light receiver is calibrated to include or coincide with that portion of the visible light spectrum which carries maximum energy.

1 Claim, 3 Drawing Figures

VISIBILITY METER AND COMPONENTS USED THEREIN

This application is a continuation of application Ser. No. 196,145, filed Oct. 10, 1980, now abandoned.

BACKGROUND OF THE INVENTION

1. Field of the Invention

This invention pertains to a visibility meter such as is used to quantify visibility in the atmosphere for, e.g., aeronautical purposes. More particularly, this invention pertains to components which can be utilized in such a visibility meter, but which may have alternative applications in other fields, in which applications the characteristics of the components can be used to advantage.

2. Description of the Prior Art

Conventional visibility meters are constructed either as forward-scatter meters, or FSM's, or as backward-scatter meters, or BSM's. Regardless of the construction of such visibility meters, it is known that the light source should advantageously have a high intensity and a high local stability of the position from which light is emitted.

Such local stability is of particularly great importance in forward-scatter meters, since such meters are so constructed that the light receiver is prevented from receiving any light from the aureole or corona of the light source. In the event that light from the aureole or corona of the light source is allowed to be incident directly upon the receiver, the output of the receiver will not be dependent upon scattering of light in the atmosphere and will therefore produce undependable measurements of visibility. Therefore, it is especially important in the case of forward-scatter meters that light produced by the light source be confined as closely as possible to a single predetermined position and have high local stability there, in order to prevent changes in location of the aureole or corona from adversely affecting accuracy.

In the prior art, a spark-gap has been used as a light source. Although such a spark-gap light source has a desirably high intensity, its local stability is low because the position of the spark may change during repeated flashings of the light source.

It has also been known to utilize a gas discharge flash tube as a light source in visibility meters. Although such gas discharge flash tubes have high local stabilities, they do not produce light of sufficient intensity.

Furthermore, it is known that light in the infrared portion of the spectrum is scattered in the atmosphere to a lesser degree than light in the visible portion of the spectrum. Hence, to the extent that the receiver in a visibility meter is permitted to respond to light in the infrared portion of the frequency spectrum, accuracy of the visibility measurement will be degraded.

Therefore, it would be advantageous to provide components for use in a visibility meter which would be so constructed that (a) the light source would have both a high intensity and a high local stability, and (b) the visibility meter would be unresponsive to light in the infrared portion of the frequency spectrum.

SUMMARY OF THE INVENTION

These objects, among others which will become apparent hereinafter, are achieved by the components with which this invention are concerned. In this invention, the light source is a discharge lamp with a discrete, hollow, gas-filled anode chamber and a discrete, hollow, gas-filled cathode chamber which are separated from each other and are interconnected via an open-ended gas-filled capillary tube. Advantageously, the gas utilized is Xenon. Furthermore, the capillary tube may advantageously extend along the optical axis of the discharge lamp and be located such that the cathode is adjacent one end of the capillary tube while the anode is located behind the other end rather than being adjacent to it.

When the lamp is used, the gas inside the capillary tube forms a plasma. This plasma is confined within the capillary tube so that local stability is high. Moreover, the lamp produces a high intensity output.

A subsidiary advantage of the light source so constructed is that, as will be explained hereinafter, blackening of the lamp caused by disintegration of the cathode does not affect the anode chamber, and consequently does not reduce light output.

The light receiver disclosed herein is so designed that its response to incident light is precisely calibrated for maximum efficiency. The light receiver utilizes a photosensitive element upon which light is focused by an optical system. The photosensitive element is connected to an electrical filter. The electrical filter is so designed that the response of the light receiver is calibrated to include or coincide with that region of the frequency spectrum which carries maximum energy. Moreover, the optical system is so constructed that infrared radiation is partially or totally blocked prior to focusing of light upon the photosensitive element. Therefore, the receiver is made unresponsive to infrared radiation.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF PREFERRED EMBODIMENTS

Figure 1:
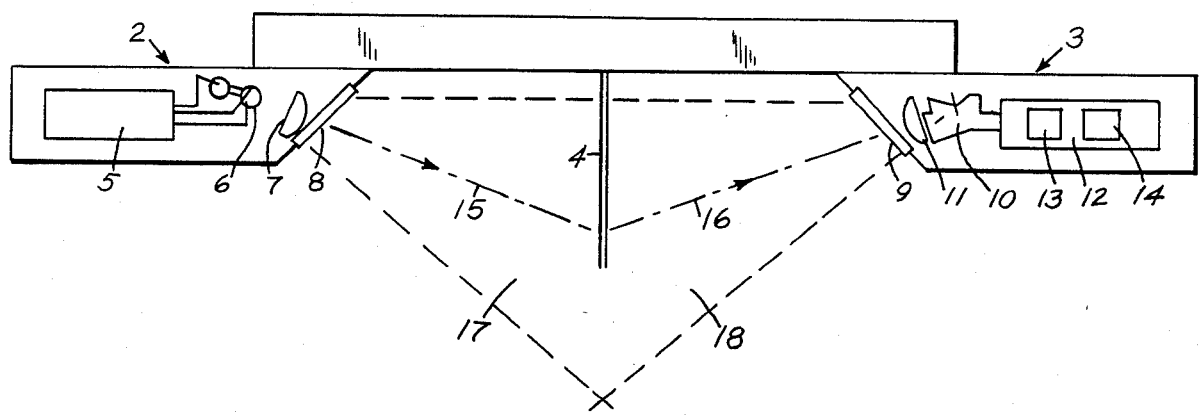
FIG. 1 shows a schematic side view of a visibility meter which utilizes the components disclosed herein.
Figure 2:
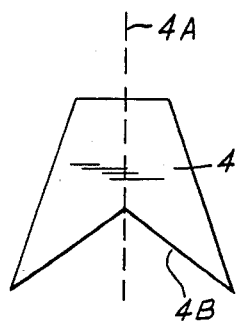
FIG. 2 shows a front view of the diaphragm utilized in the visibility meter depicted in FIG. 1.

Referring first to FIG. 1, it can be seen that a carrier 1 supports a light transmitter 2 at one end and a light receiver 3 at another end. A diaphragm 4 extends downwardly between light transmitter 2 and light receiver 3.

Those skilled in the art will readily appreciate that it is undesirable for any light from light transmitter 2 to be directly incident upon light receiver 3, since such direct incidence will cause light receiver 3 to generate an output which does not reflect light scattering in the atmosphere and which therefore does not reflect visibility. In order to prevent such direct incidence from taking place, light transmitter 2 utilizes a highly directional discharge lamp generally indicated in FIG. 1 by reference numeral 6 as a light source. Moreover, diaphragm 4 extends not only downwardly but outwardly, to form a divided member which is symmetrical about vertical axis 4A and has a V-shaped notch 4B which faces downwardly.

Light from transmitter 2 is projected downwardly along a line indicated by reference numeral 15 in FIG. 1. Conversely, in order for light to enter light receiver 3, such light would have to be oriented along a line indicated by reference numeral 16 in FIG. 1. As can be seen in FIG. 1, diaphragm 4 extends downwardly and outwardly to such a degree that any direct transmission of light from transmitter 2 to receiver 3 is completely blocked. However, as can also be seen from FIG. 1, light from transmitter 2 which falls within a cone indicated by reference numeral 17 can be reflected off moisture particles in the atmosphere and thereby made to approach light receiver 3 by travelling through a cone indicated by reference numeral 18. Hence, although direct incidence of light from light transmitter 2 to light receiver 3 is prevented by diaphragm 4, indirect incidence caused by reflection off moisture particles in the atmosphere can and does take place. Since such reflection is a function of cloudiness, it is also a measure of visibility. Thus, output of light receiver 3 will provide an accurate indication of visibility in the atmosphere in which it is located.

Figure 3:
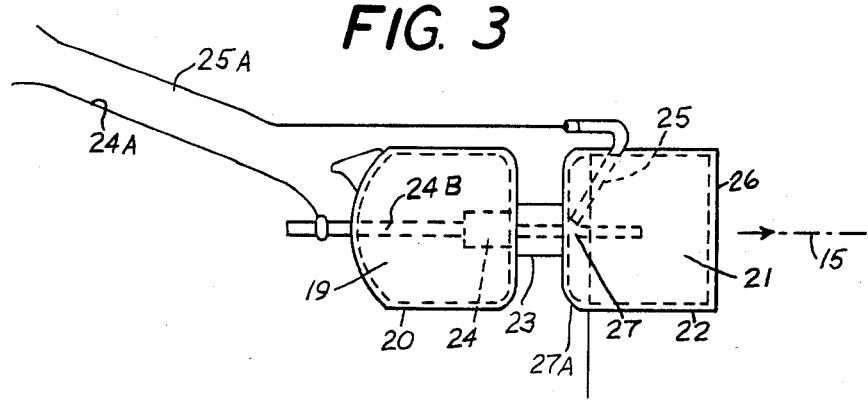
FIG. 3 shows a side view of the discharge lamp used as a light source in the visibility meter depicted in FIG. 1, in which side view hidden elements and hidden lines are dotted.

Light transmitter 2 contains a light source indicated by reference numeral 6 in FIG. 1 and shown in more detail in FIG. 3. Light source 6 is powered by power source 5. Light from light source 6 is directed through an optical system which may include one or more lenses and which is schematically shown as lens 7. After passing through lens 7, light from light source 6 passes through window 8 and thence into the atmosphere for reflection from moisture particles therein as has been set forth above.

Turning now to FIG. 3, which shows light source 6 in more detail, it can be seen that a hollow cathode chamber 19 formed by housing 20 contains a cathode 24, which is connected to a power line 24A via rod 24B, which rod 24B passes through housing 20. Power line 24A is connected to power source 5.

In a similar fashion, anode 25 is contained within anode chamber 21 which is formed by housing 22. Anode 25 is a bent electrode which passes through housing 22 and is connected to power line 25A, and is thus connected to power source 5. Front surface 26 of housing 22 is flattened to form a window from which light will exit along a line indicated by reference numeral 15, which appears in both FIG. 1 and FIG. 3.

Housings 20 and 22 are physically connected together by neck 23A, so that they are physically fixed relative to each other. Moreover, cathode chamber 19 and anode chamber 21 are interconnected by capillary tube 23, which has one end attached to housing 20 so as to open up directly into the forwardmost end of cathode chamber 19. Capillary tube 23 enters anode chamber 21 adjacent anode 25, and continues into anode chamber 21 so that its forwardmost end is located closer to surface 26 than is anode 25.

Cathode chamber 19 and anode chamber 21 are filled with gas, which advantageously may be Xenon. In order to cause an electrical discharge between anode 25 and cathode 24, a trigger means which may preferably take the form of a wire electrode 27 is wrapped around housing 22 adjacent region 27A. Region 27A is a region where anode 25 adjoins capillary tube 23 at the rearwardmost end of anode chamber 21.

As can be seen in FIG. 3, cathode 24 adjoins one end of capillary tube 23 within cathode chamber 19. When approximately 600 volts are placed across power lines 24A and 25A by power source 5, and when a trigger voltage is applied to wire electrode 27, a plasma will form within capillary tube 23, and thus within a fixed location. Therefore, the local stability of the discharge lamp so formed is adequately high. Moreover, light output is adequately intense. The optical axis of light source 6 is defined by the axis of capillary tube 23, and is aligned with the line identified by reference numeral 15. Surface 26 is perpendicular to capillary tube 23, and is thus perpendicular to the optical axis of light source 6.

As can be seen in FIG. 3, both cathode chamber 19 and anode chamber 21 are discrete, and are in communication with each other only via capillary tube 23. As a result, disintegration of cathode 24 which takes place during use and which ordinarily causes a diminution of light output by blackening of surfaces through which light passes cannot take place. Such blackening, to the extent that it occurs, takes place only within cathode chamber 19 and has no effect upon anode chamber 21. Thus, blackening caused by disintegration of cathode 24 does not adversely affect light output from light source 6.

If Xenon gas is utilized, usage of light source 6 in environments below −38° C. cannot take place without additional precautions being implemented. Below −38° C., Xenon enters a vapor phase. Therefore, in the event that light source 6 is to be utilized in environments below this temperature, it is necessary to heat light source 6 using a suitable heater, so that light source 6 is always maintained above this temperature and will operate properly.

Light entering light receiver 3 first passes through window 9, and thence reaches an optical system which may include one or more lenses and which is schematically indicated as lens 11. Lens 11 focuses light passing into light receiver 3 onto photosensitive element 10, which may advantageously be a silicon photodiode. Photosensitive element 10 is connected to electrical filter 13, which forms a component within switching system 12. Switching system 12 also contains switch 14, which switch 14 may advantageously be an AND-gate which reduces or cuts off current flowing through photosensitive element 10 inbetween flashes of light emitted by light source 6, in a fashion already known from Swiss Pat. No. 566 013.

Electrical filter 13 is provided in order to pass to switch 14 optimum frequency bands of electrical pulses corresponding to received light flashes from the discharge lamp 6. In order to accomplish this function, electrical filter 13 may be constructed as a high-pass filter with its cutoff frequency set closely below a lower boundary of a frequency band of the frequency spectrum of the electrical pulses within which maximum energy is carried. Alternatively, electrical filter 13 may be constructed as a bandpass filter in which its bandpass characteristics are set to coincide with this frequency band of the frequency spectrum in which the electrical pulse carries a maximum energy. The lowest cutoff frequency for electrical filter 13 will be at least 10 kHz and will be preferably 20 kHz. If electrical filter 13 is constructed as a bandpass filter, its upper cutoff frequency will advantageously be set at approximately 300 kHz. In this manner, the response of light receiver 3 to interference caused by passing motor vehicles or by passing clouds is reduced.

The frequency spectrum of light from light source 6 contains an infrared component, albeit a small one. In order to prevent such infrared component from being registered at photosensitive element 10, windows 8 or 9, and preferably window 9, can be manufactured as infrared filters. Alternatively, or additionally, lenses 7 or 11 or both may be manufactured of a material which absorbs infrared radiation.

It will be understood that each of the elements described above, or two or more together, may also find a useful application in other types of constructions differing from the types described above.

While the invention has been illustrated and described as embodied in a visibility meter and components used therein, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A visibility meter using a forward scatter of light pulses in an atmospheric sample, comprising a pulse light transmitter for transmitting a downwards directed beam of light pulses and having a light source in the form of a point-shaped, end-on capillary spark; a light receiver arranged opposite said transmitter; and a V-shaped heated diaphragm being arranged between said transmitter and receiver to interrupt optical contact therebetween.

* * * * *